US00PP37450P2

(12) United States Plant Patent
Grazzini

(10) Patent No.: US PP37,450 P2
(45) Date of Patent: Jun. 2, 2026

(54) *COLEUS* PLANT NAMED 'G21015'

(50) Latin Name: *Coleus scutellarioides*
Varietal Denomination: G21015

(71) Applicant: Garden Genetics llc, Columbus, OH (US)

(72) Inventor: Richard A. Grazzini, Columbus, OH (US)

(73) Assignee: Garden Genetics, Columbus, OH (US)

( * ) Notice: Subject to any disclaimer, the term of this patent is extended or adjusted under 35 U.S.C. 154(b) by 0 days.

(21) Appl. No.: 19/354,397

(22) Filed: Oct. 9, 2025

(51) Int. Cl.
*A01H 5/02* (2018.01)
*A01H 6/50* (2018.01)

(52) U.S. Cl.
USPC ..... Plt./469

(58) Field of Classification Search
USPC ..... Plt./263.1, 469
See application file for complete search history.

(56) References Cited

U.S. PATENT DOCUMENTS

PP32,342 P2 * 10/2020 Solano Ramirez ..... A01H 6/50
Plt./373

* cited by examiner

*Primary Examiner* — Karen M Redden

(57) ABSTRACT

A new and distinct cultivar of *Coleus* plant named 'G21015' is disclosed, characterized by a compact, densely branched plant habit forming a globose shape. Foliage is dark burgundy red in the central area, surrounded by a thick gold-green picotee edge and a fine dark burgundy red margin. Floral initiation begins in early October, or later at 41N latitude, under natural daylength. Foliage is strongly resistant to *Coleus* downy mildew (CDM), caused by *Peronospora choii*. No symptoms of CDM have been observed on new variety 'G21015' since its selection in 2021 in greenhouse, outdoor container, or outdoor in-ground trials. In those same trials, CDM-susceptible *Coleus* varieties were observed to suffer foliage losses due to CDM infection at rates from 25% to 100%. The new cultivar is a *Coleus*, typically produced as an outdoor ornamental plant or for garden or container uses.

2 Drawing Sheets

Figure 1:
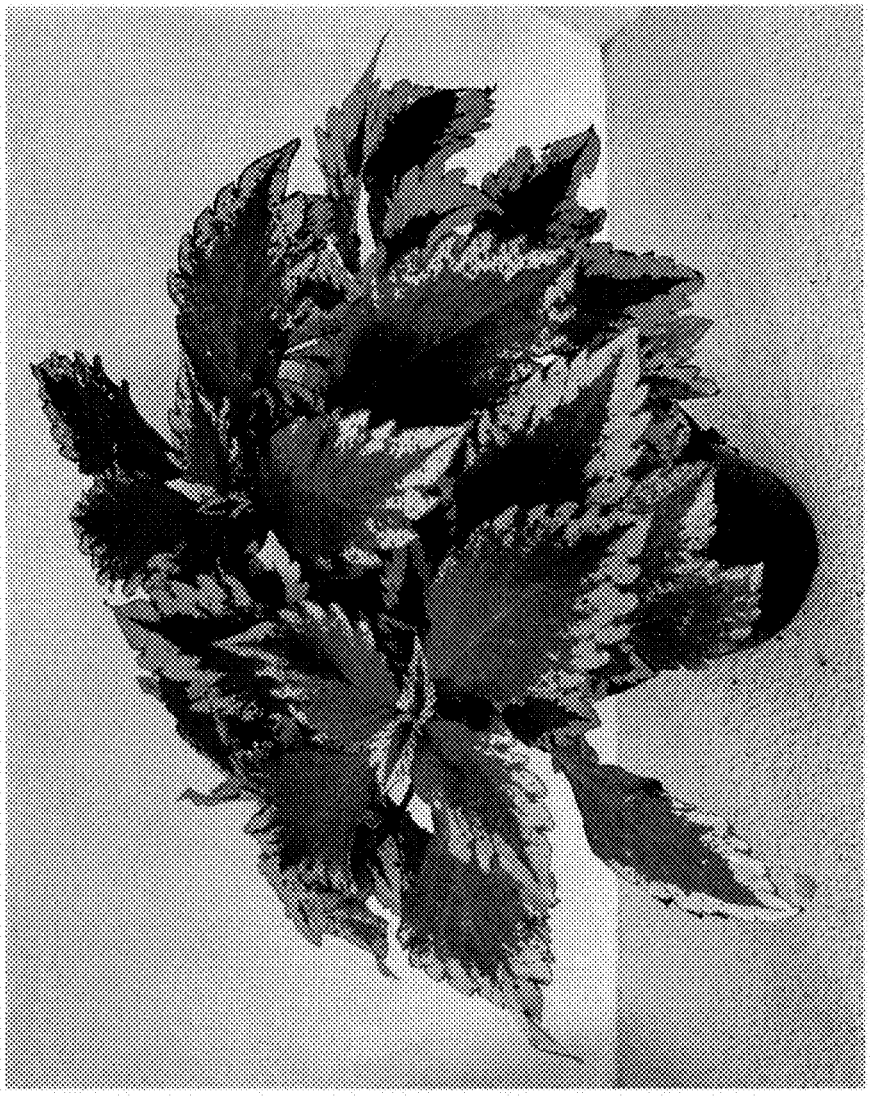

Latin name of the genus and species: *Coleus scutellarioides.*

Variety denomination: 'G21015'.

BACKGROUND OF THE INVENTION

The new cultivar is the product of a planned breeding program conducted by the inventor. The cross-pollination resulting in the new variety was made in August of 2020 at a research greenhouse in Bellefonte, Pennsylvania. The seed parent is an undistributed, unpatented proprietary F1 seedling variety referred to internally as G18-206-5. The pollen is an undistributed, unpatented proprietary F1 seedling variety referred to internally as G20-049. The new variety was found and selected by the inventor in March of 2021 at the same research greenhouse in Bellefonte, Pennsylvania.

Asexual reproduction of the new cultivar 'G21015' by terminal vegetative cuttings was performed at the same nursery in Bellefonte, Pennsylvania in March of 2021. Subsequent asexual reproduction, both by terminal cuttings and tissue culture has shown that the unique features of this cultivar are stable and reproduced true to type through successive generations.

SUMMARY OF THE INVENTION

The cultivar 'G21015' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'G21015'. These characteristics in combination distinguish 'G21015' as a new and distinct *Coleus* cultivar:

1. Compact, uniform, densely branched habit.
2. Plant is typically a globe shape, 20 to 22 in (51 to 56 cm) in both height and width.
3. Foliage is dark burgundy red in the central area, surrounded by a thick gold-green picotee edge and a fine dark burgundy red margin.
4. Foliage is strongly resistant to *Coleus* downy mildew (CDM), caused by *Peronospora choii.*

No symptoms of CDM have been observed on new variety 'G21015' since its selection in 2021 in greenhouse, outdoor container, or outdoor in-ground trials. In those same trials, CDM-susceptible *Coleus* varieties were observed to suffer foliage losses due to CDM infection at rates from 25% to 100%.

PARENT COMPARISON

Plants of the new cultivar 'G21015' are similar to plants of the seed parent variety, in most horticultural characteristics. However, plants of the new cultivar 'G21015' differ in the following:

1. 'G21015' is less compact and less densely branched than the seed parent. 'G21015' forms a globe 20 to 22 inches (51 to 56 cm) in both height and width. A typical plant of the seed parent is a smaller globe, 15 to 18 inches (38 to 46 cm) in diameter.

2. 'G21015' has larger leaves than the seed parent. Leaves of 'G21015' are typically 25 to 30% larger in size (width and length) than leaves of the seed parent.
3. 'G21015' exhibits stronger field-tolerance to the pathogen *Coleus* downy mildew (CDM), caused by *Peronospora choii* than the seed parent. 'G21015' typically shows no sign of CDM infection, whereas the seed parent will typically lose 25 to 30% of its lowermost foliage to CDM infection.
4. 'G21015' flowers much later than the seed parent. At 41N latitude, grown outdoors under natural daylengths, new variety 'G21015' does not show flower buds on 1 October, whereas the seed parent typically begins to flower in the first week of September.

Plants of the new cultivar 'G21015' are similar to plants of the pollen parent variety, in most horticultural characteristics. However, plants of the new cultivar 'G21015' differ in the following:

1. 'G21015' is less compact, more densely branched, and less upright in habit than pollen parent G20-049. 'G21015' forms a globe 20 to 22 inches (51 to 56 cm) in both height and width. A typical plant of pollen parent G20-049 is an upright globe, 15 to 18 inches (38 to 46 cm) in width and 22 to 24 inches (56 to 61 cm) in height.
2. 'G21015' has larger leaves than the pollen parent. Leaves of 'G21015' are typically 25 to 30% larger in size (width and length) than foliage of the pollen parent.
3. 'G21015' exhibits stronger field-tolerance to the pathogen *Coleus* downy mildew (CDM), caused by *Peronospora choii* than pollen parent G20-049. 'G21015' typically shows no sign of CDM infection, whereas pollen parent G20-049 will typically lose 25% or more of its lowermost foliage to CDM infection.
4. 'G21015' flowers much later than pollen parent G20-049. At 41N latitude, grown outdoors under natural daylengths, new variety 'G21015' typically does not show flower buds on 1 October, whereas pollen parent G20-049 typically begins to flower in the first week of September.

COMMERCIAL COMPARISON

'G21015' can be compared to the commercially known variety *Coleus* 'Apple Brandy', unpatented. These plants are similar in most horticultural characteristics. However, plants of the new cultivar 'G21015' differ in the following ways:

1. 'G21015' is more vigorous and less compact than 'Apple Brandy'.
2. 'G21015' has more larger foliage than 'Apple Brandy'.
3. 'G21015' has more consistent marginal gold picotee leaf edge than 'Apple Brandy'.
4. 'G21015' blooms about 4 weeks later than 'Apple Brandy' at 41N latitude, natural daylength
5. 'G21015' exhibits much stronger resistance/tolerance to *Coleus* downy mildew (CDM) caused by *Peronospora choii* than this comparator.

'G21015' can also be compared to the commercially known variety *Coleus* 'Balflamsira', U.S. Plant Pat. No. 32,342. These cultivars are similar in most horticultural characteristics. However, plants of the new cultivar 'G21015' differ in the following ways:

1. 'G21015' is more vigorous and less compact than 'Balflamsira'.
2. 'G21015' has larger foliage than 'Balflamsira'.
3. 'G21015' has a more sharply defined marginal gold picotee leaf edge than 'Balflamsira'.
4. 'G21015' blooms about 2 to 3 weeks later than 'Balflamsira' at 41N latitude, natural daylength
5. The central blotch of leaves of 'G21015' a darker-violet in color than those of the 'Balflamsira', which are more red-violet in color.

BRIEF DESCRIPTION OF THE PHOTOGRAPHS

The accompanying photograph in FIG. 1. illustrates a typical plant of 'G21015' grown outdoors in Camarillo, CA. The plant is approximately 4 months old from a rooted cutting, in a one-gallon pot.

Figure 2:
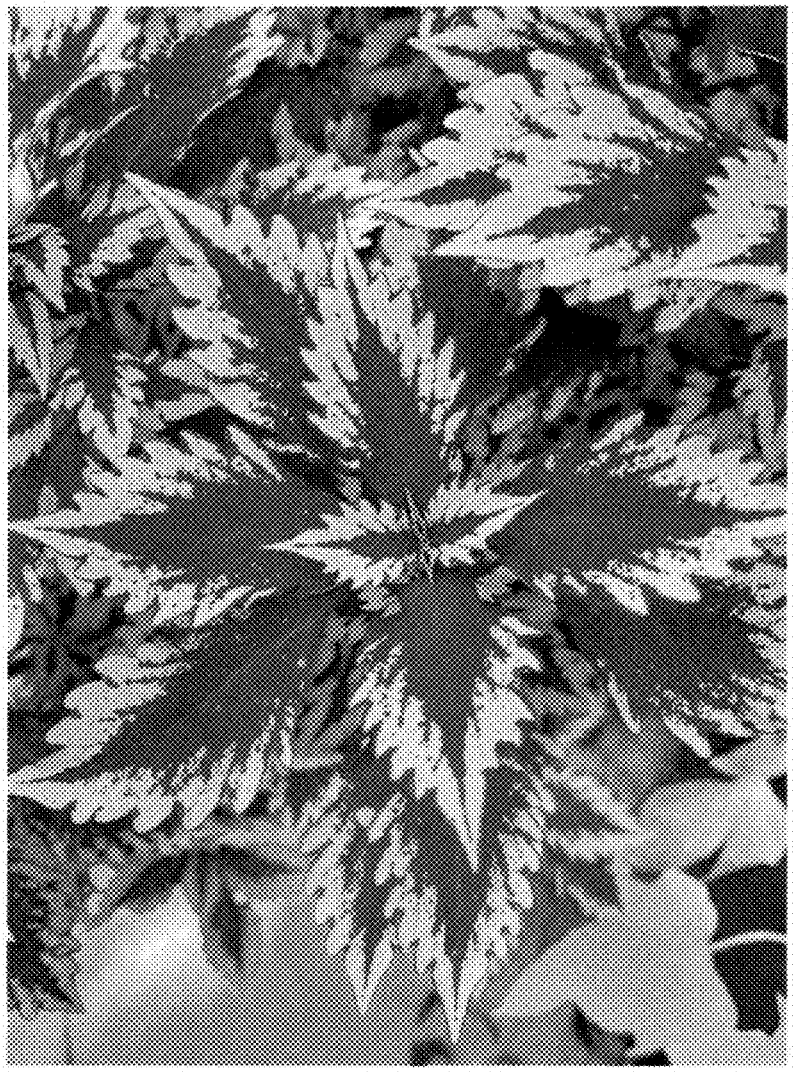

FIG. 2 illustrates a close-up view of the mature foliage on a plant of about 5 months old grown in Columbus, OH.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Color Chart 2015, except where general terms of ordinary dictionary significance are used. The following observations and measurements describe 'G21015' plants grown outdoors during Summer in Camarillo, California. The growing temperature ranged from about 7° C. to 28° C. during the day and from about 5° C. to 18° C. during the night. General light conditions are bright, normal sunlight. Measurements and numerical values represent averages of typical plant types. Plants are approximately 4 months old from a rooted cutting. No chemical or photoperiodic treatments were given.

Botanical classification: *Coleus scutellarioides* 'G21015'.

PROPAGATION

Root description: Fine, well-branched, fibrous, becoming slightly woody with age. Colored near Greyed-Yellow-161D and White 155A.

PLANT

Growth habit: Tender herbaceous perennial. Upright.
Height: Approximately 30 cm.
Plant spread: Approximately 32 cm.
Branching characteristics: Basal and lateral branching.
Length of branches: Approximately 9 to 22 cm.
Diameter branches: Approximately 5 to 6 mm.
Quantity of branches: Approximately 4 to 6 basal branches, each basal branch with 4 to 5 lateral branches.
Texture of lateral branches: Puberulent and ridged.
Color of lateral branches:
*Upper surface*.—Greyed-Purple 187D. Puberulent layer Greyed-Purple N187D.
*Lower surface*.—Greyed-Purple 187D. Puberulent layer Greyed-Purple N187D. Infrequent streaks Yellow-Green 144C.
Aspect: Approximately 20° to 45° angle from center of plant.
Strength of lateral branches: Moderate. Not easily broken, no brittleness.

Internode length: Average range 1.8 to 35 cm.
Age of plant described: Approximately 4 months old.

FOLIAGE

Arrangement: Opposite.
Average length: 9 cm.
Average width: 5 cm.
Shape of blade: Ovate.
Apex: Acute.
Base: Rounded.
Attachment: Petiolate.
Margin: Serrate. Serrations 5 to 10 mm deep.
Texture of top surface: Soft, velvety.
Texture of bottom surface: Non-pubescent with protruding veins.
Foliage color:
*Young foliage upper side.*—Greyed-Purple 187B tinged Greyed-Orange 176A over 50 to 85% of the leaf surface. Changes from center to margin in a serrated pattern to Yellow-Green 144C. Some speckling in the yellow-green section 187B. Margin 187B.
*Young foliage under side.*—Yellow-Green N144D. Faint central blotch, covering about 50% to 85% of the blade, shaped like the leaf blade colored N186C. Some speckling outside of the blotch also N186C.
*Mature foliage upper side.*—Greyed-Purple 187C over 50 to 85% of the leaf surface. Changes from center to margin in a serrated pattern to Yellow-Green 144C, forming a distinct, thick picotee edge. Some speckling in the yellow-green section 187B. The outermost margin is a thing line of 187C.
*Mature foliage under side.*—Yellow-Green N144D. Faint central blotch, covering about 50% to 85% of the blade, shaped like the leaf blade colored N186C. Some speckling outside of the blotch also N186C.
Venation:
*Type.*—Pinnate. Venation color upper side: Greyed-Purple 187D. Near apex Green N144D. Venation color under side: Lower half near Greyed-Purple 185C. Upper half Yellow-Green 145C flushed 185D.
Petiole:
*Length.*—Average range 2 to 5.
*Diameter.*—Average 4 mm.
*Color.*—Upper: Yellow-Green 144C flushed Greyed-Purple 184C. Lower: Yellow-Green 144C flushed Greyed-Purple 186D.
*Texture.*—Glabrous.
INFLORESCENCE
Natural flowering season: Floral initiation may begin in October. Flowering may not be observed every year.
Inflorescence type and habit: Terminal raceme.
Individual flowers: Zygomorphic flowers facing outward.
Longevity of individual flowers: About 3 weeks.
Fragrance: None
Inflorescence size:
*Length.*—5 to 10 cm.
*Width.*—4 cm.
Quantity of flowers per inflorescence: About 10 to 30.
Corolla:
*Shape.*—Bilabiate, tubular.
*Aspect.*—Outward.
*Persistence.*—Self-cleaning.
*Size.*—About 15 mm long and 5 mm wide.
Petals:
*Upper lip.*—Width: 7 mm. Length: 5 mm. Apex: Obtuse, rounded, composed of 2 fused lobes. Base: Fused to central petal. Margin: Entire. Texture: Front: Glabrous. Back: Glabrous. Color: Upper surface: RHS Violet-Blue 91D. Lower surface: RHS Violet-Blue 91D.
*Lower lip.*—Width: 5 mm (folded). Length: 1 cm. Apex: Obtuse, rounded. Base: Fused. Margin: Entire. Texture: Front: Glabrous. Back: Glabrous. Color: Upper surface: RHS Violet-Blue N89C. Base 91D. Lower surface: RHS Violet-Blue 90D. Base White N155A.
*Tube.*—Diameter: 3 mm. Length: 5 mm. Color: Inner: RHS Violet-Blue 91D. Outer: RHS Violet-Blue 91D. Glabrous. 8 Texture:
Bud:
*Shape.*—Ovate.
*Color.*—Base Violet-Blue 91D, apex 90A.
*Size.*—5 mm in height and 4 mm in diameter.
*Texture.*—Glabrous.
Calyx: Bell-shaped, composed of 5 sepals fused at base.
Sepals:
*Shape.*—Elliptic.
*Apex.*—Acute.
*Base.*—Fused.
*Margin.*—Entire.
*Length.*—5 mm.
*Width.*—3 mm.
*Texture.*—Glabrous, upper and lower surfaces.
*Color.*—Upper surface: RHS Yellow-Green 145A. Lower surface: RHS Yellow-Green 145B.
Peduncle:
*Shape.*—Quadrate with prominent longitudinal veins.
*Length.*—2 to 5 cm.
*Diameter.*—4 mm.
*Strength.*—Medium.
*Texture.*—Glabrous.
*Color.*—RHS Yellow-Green N144D.
Pedicel:
*Orientation.*—45° to 90° from peduncle.
*Texture.*—Glabrous.
*Length.*—5 to 7 mm.
*Diameter.*—2 mm.
*Color.*—RHS Yellow-Green 144B.
*Strength.*—Medium.

REPRODUCTIVE ORGANS

Androecium:
*Number of stamens.*—4 per flower, non-protruding.
*Filament.*—Unfused segment about 4 mm, colored near White N155C.
*Pollen.*—Not observed.
Gynoecium:
*Pistil number.*—1 per flower.
*Pistil length.*—15 mm.
*Style length.*—8 mm.
*Style color.*—RHS White N155C.
*Stigma shape.*—Two-parted.
*Stigma color.*—White N155C.
*Ovary color.*—RHS Yellow-Green N144D.

OTHER CHARACTERISTICS

Disease resistance: Foliage is strongly resistant to *Coleus* downy mildew (CDM), caused by *Peronospora choii*. No symptoms of CDM have been observed on new variety 'G21015' since its selection in 2021 in greenhouse, outdoor container, or outdoor in-ground trials. In those same trials, CDM-susceptible *Coleus* varieties were observed to suffer foliage losses due to CDM infection at rates from 25% to 100%. Neither resistance nor susceptibility to other diseases or to pests normal to *Coleus* have been observed in this cultivar.

Drought tolerance and temperature tolerance: No tolerance for drought. Tender perennial, USDA zones 10-11. Summer annual in colder zones.

Fruit/seed production: Not observed to date.

What is claimed is:

1. A new and distinct cultivar of *Coleus* plant named 'G21015' as herein illustrated and described.

* * * * *